US007320891B2

(12) United States Patent
Tereba et al.

(10) Patent No.: US 7,320,891 B2
(45) Date of Patent: Jan. 22, 2008

(54) METHODS AND KITS FOR ISOLATING SPERM CELLS

(75) Inventors: Allan Tereba, Fitchburg, WI (US); Laura Flanagan, Madison, WI (US); Paraj Mandrekar, Oregon, WI (US); Ryan Olson, Madison, WI (US)

(73) Assignee: Promega Corporation, Madison, WI (US)

( * ) Notice: Subject to any disclaimer, the term of this patent is extended or adjusted under 35 U.S.C. 154(b) by 404 days.

(21) Appl. No.: 10/939,105

(22) Filed: Sep. 10, 2004

(65) Prior Publication Data

US 2006/0057715 A1    Mar. 16, 2006

(51) Int. Cl.
*C12N 5/00* (2006.01)
(52) U.S. Cl. .......................... 435/325; 435/2; 435/366
(58) Field of Classification Search .................... 435/2, 435/325, 366
See application file for complete search history.

(56) References Cited

U.S. PATENT DOCUMENTS

| | | | |
|---|---|---|---|
| 4,900,685 A | 2/1990 | Smith, III | |
| 5,116,496 A | 5/1992 | Scott | |
| 5,130,423 A * | 7/1992 | Van Ness et al. | 536/25.42 |
| 5,275,731 A | 1/1994 | Jahn et al. | |
| 5,464,541 A | 11/1995 | Aysta et al. | |
| 5,494,800 A | 2/1996 | Smith, III | |
| 5,495,800 A | 3/1996 | Weissbein et al. | |
| 5,672,579 A | 9/1997 | Diaz et al. | |
| 5,741,423 A | 4/1998 | Bates et al. | |
| 5,746,836 A | 5/1998 | Fukai | |
| 5,755,987 A | 5/1998 | Goldstein et al. | |
| 5,766,632 A | 6/1998 | Oldham et al. | |
| 5,840,771 A | 11/1998 | Oldham et al. | |
| 5,916,857 A * | 6/1999 | Watson et al. | 510/174 |
| 6,291,179 B1 | 9/2001 | Burgoyne | |
| 6,368,777 B1 | 4/2002 | Obuchowicz | |
| 6,544,942 B1 | 4/2003 | Smith et al. | |
| 6,689,615 B1 | 2/2004 | Murto et al. | |
| 2002/0077376 A1 | 6/2002 | Usui et al. | |
| 2002/0182751 A1 | 12/2002 | Herr et al. | |
| 2003/0021853 A1 | 1/2003 | Wei et al. | |
| 2003/0215845 A1 | 11/2003 | Bille | |
| 2003/0215956 A1 | 11/2003 | Reed | |

FOREIGN PATENT DOCUMENTS

| | | |
|---|---|---|
| EP | 0 648 820 A3 | 4/1995 |
| EP | 0 559 777 B1 | 2/2000 |
| EP | 0 902 801 B1 | 8/2001 |
| WO | WO 95/09641 | 4/1995 |
| WO | WO 01/12847 A2 | 2/2001 |
| WO | WO 01/35759 A1 | 5/2001 |
| WO | WO 01/52968 A1 | 7/2001 |
| WO | WO 01/95951 A1 | 12/2001 |
| WO | WO 00/77251 A2 | 12/2002 |
| WO | WO 03/070898 A3 | 8/2003 |

OTHER PUBLICATIONS

Bryant, JC. Earle's balanced salt solution: preparation of the saline. 1975. 1(4): 185-187.*

Yoshida, K et al. The modified method of two-step differential extraction of sperm and vaginal epithelial cell DNA from vaginal fluid mixed with semen. Forensic Science International. 1995. 72(1): 25-33.*

"Laboratory Solvents and Other Liquid Reagents", in CRC Handbook of Chemistry and Physics, Internet Version 2007, (87th Edition), David R. Lide, ed., Taylor and Francis, Boca Raton, FL.*

"Percoll density gradient medium for purification of cells, organelles and viruses" Amersham Biosciences, http://www.cellseparation.nu/percoll.html. Jul. 12, 2004.

Bolton, et al. "Removal of bacterial contaminents from semen for in vitro fertilization or artificial insemination by the use of buoyant density centrifugation" Fertil Steril, Dec.;46(6):1128-32 (1986).

Bolton, VN, and Braude, PR, "Preparation of human spermatozoa for in vitro fertilization by isopycnic centrifugation on self-generating density gradients" Archives of Andrology 13:167-176 (1984).

Comey, et al., "DNA Extraction Strategies for Amplified Fragment Length Polymorphism Analysis" J Forensic Sciences, 39(5):1254-1269 (1994).

DiNunno, et al. "DNA identification of sperm cells collected and sorted by the flow cytometry" Am J. Forensic Med Pathol Sep. ;24(3):254-70 (2003).

Garvin, A.M., "Filtration based DNA preparation for sexual assault cases" J Forensic Sci, Sep.;48(5):1084-7 (2003).

Genomes, 2nd Edition, "2.2 The Anatomy of the Eukaryotic Genome: Ultracentrifugation techniques" Bios Scientific Publishers, Ltd. (1999).

Gill, P. et al., "Forensic Application of DNA 'Fingerprints'," *Nature* (1985) 318:577-579.

Henkel, RR, and Schill, W, "Sperm preparation for ART" Reproductive Biology and Endocrinology, 108:1-22 (2003).

Landers, et al., "Isolation of sperm cells from other cells in cell mixtures" University of Virginia Patent Foundation, 2 pgs. www.avapf.org/technologies/index.cfm/fuseaction/invention/invention_id/180/?CFID Aug. 9, 2004.

Ord, et al., "Mini-Percoll: a new method of semen preparation for IVF in severe male factor infertility" Human Reproduction, 5(8):987-989 (1990).

OSHA Technical Links, Sampling & Analytical Methods, Index, Dimethyl Glutarate 12 pgs. Sep. 1995.

(Continued)

*Primary Examiner*—Leon B. Lankford, Jr.
*Assistant Examiner*—Susan E. Fernandez
(74) *Attorney, Agent, or Firm*—Michael Best & Friedrich LLP

(57) ABSTRACT

Disclosed are methods for isolating sperm cells from an aqueous sample and kits for isolating sperm cells from an aqueous sample.

19 Claims, 1 Drawing Sheet

OTHER PUBLICATIONS

PERCOLL Methodology and Applications, Amersham Biosciences, 8 pgs. (2002).

Promega "Differex™ System" TBD020 1-7, (2004).

Promega "DNA IQ™ System-Small Sample Casework Protocol" TB296, 1-11, Rev. Jun. 2002.

Sanders, et al. "A simple PDMS-based electro-fluidic interface for microchip electrophoretic separations" Analyst, 127(12):1558-1563 (2002).

Schoell, et al. "Separation of sperm and vaginal cells based on ploidy, MHC class I -, CD45 -, and cytokeratin expression for enhancement of DNA typing after sexual assault" Cytometry, 36(4):319-323 (1999).

Schuster, et al., "Isolation of motile spermatozoa from semen samples suing microfluidics" Reprod Biomed Online, Jul.-Aug.;7 (1):75-81 (2003).

Tucker, KE, and Jansen, Cam, "Sperm separation techniques: comparison and evaluation of gradient products" Proceedings 2nd International Workshop for Embryologists: Troubleshooting, Activities in the ART lab. Ed., R. Basuray and D. Mortimer, 1-7, 2002 (in press).

Walsh, et al., "Chelex 100 as a medium for simple extraction of DNA for PCT-based typing from forensic material" Biotechniques Apr.;10(4):506-13 (1991).

Weinberger, Robert, "Guest Editorial, Meeting Review: The 14th Annual Frederick Conference on Capillary Electrophoresis", American Laboratory, Feb. 4-8 (2004).

Wiegand, et al., "DNA extraction from mixtures of body fluid using mild preferential lysis" Int J Leg Med 104:359-360 (1992).

Iwasa, M. et al., "Y-chromosomal short tandem repeats haplotyping from vaginal swabs using a chelating resin-based DNA extraction method and a dual-round polymerase chain reaction," Am. J. Forensic Med. Path. (2003) 24(3):303-305.

Tsuji, A. et al., "Personal identification using Y-chromosomal short tandem repeats from bodily fluids mixed with semen," Am. J. Forensic Med. Path. (2001) 22(3):288-291.

* cited by examiner

METHODS AND KITS FOR ISOLATING SPERM CELLS

Genetic material obtained from forensic samples can be used to identify perpetrators of sexual assaults or to exonerate innocent suspects. Purified DNA obtained from sperm cells isolated from forensic samples can be used in subsequent genetic identity testing. The genetic profile of sperm cell DNA can be compared to that of a known suspect or to databases containing genetic information about a large number of convicted felons.

In sexual assault cases, a vaginal or rectal swab, or clothing containing a semen stain, is obtained from the victim for forensic analysis. If sperm cells are present in the sample, DNA from the sperm cells can be isolated and used in genetic identity testing. However, a vaginal swab obtained from a sexual assault victim typically contains relatively few sperm cells and large numbers of epithelial cells from the victim. As a consequence, unless the sperm cells are first separated from other cells in the sample, DNA purified from a forensic sample is susceptible to overwhelming contamination with epithelial cell DNA. Contamination with epithelial cell DNA interferes with the ability to establish a match between the genetic profile of DNA from the sample and that of the suspect or a member of the database. It is therefore desirable to isolate sperm cells from other cells in a forensic sample prior to DNA isolation and analysis.

Techniques currently used to isolate sperm cells from other cells in forensic samples are time consuming and labor intensive, and there is currently a backlog of unprocessed samples. Because of this backlog, some jurisdictions have a policy against processing samples unless a suspect has been identified. Consequently, many unprocessed samples are ultimately discarded, and genetic information contained in the sample is never compared with or entered into the national database, which reduces the ability of law enforcement to identify and apprehend repeat sex offenders.

Sperm cells are typically isolated from forensic samples containing epithelial cells by selectively lysing the epithelial cells by treatment with Proteinase K and a detergent under nonreducing conditions (Gill et al. 1985). Following epithelial cell lysis, intact sperm cells are pelleted by centrifugation and the supernatant, which contains DNA from lysed epithelial cells, is removed. In order to minimize contamination by soluble epithelial cell DNA, the sperm pellet is subjected to repeated washing with an aqueous buffer in an attempt to remove soluble epithelial cell DNA. This process frequently results in the loss of sperm cells.

Sperm cells have been isolated from samples containing both sperm and epithelial cells by selectively binding the sperm cells to sperm cell specific polyclonal or monoclonal antibodies attached to a solid support (e.g., paramagnetic particles). After binding the cells to the immobilized antibodies, the support is washed to remove unbound cells. This method requires a large amount of antibodies and is therefore relatively expensive. Furthermore, sperm cells are lost during the wash steps, resulting in reduced yield. Because sperm cells undergo structural changes in the relatively low pH of the vagina, many sperm cell-specific antibodies do not bind to sperm cells from all semen-containing samples. In addition, antibodies may not bind efficiently because of variations or mutations in sperm cell surface antigens in certain individuals, resulting in poor sperm cell yields.

Sperm cells may be separated from epithelial cells on the basis of differences in cell size by filtering the sample through size selective membranes. This method is problematic because sperm cells tend to become trapped among the epithelial cells, the sperm cells form clumps that are too large to pass through the membrane, and the membrane tends to clog, which ultimately may result in low yields of sperm cells contaminated with epithelial cells or epithelial cell DNA.

In another method, sperm cells are isolated by first selectively lysing epithelial cells and filtering the lysate to effect separation of the soluble epithelial cell DNA and intact sperm cells. However, the method suffers from disadvantages, including clogging of the membrane, low sperm cell yields and contamination of the sperm cells with epithelial cell DNA.

In the field of reproductive medicine, sperm cells have been isolated from fresh semen using a cell sorter, which although effective, is not practical in the forensic context because it is costly, time consuming, and does not address how to effectively recover sperm cells and epithelial cells from a forensic sample (e.g., a swab or clothing).

Thus, there is a need in the art for simplified methods of separating sperm cells from epithelial cells in forensic samples.

SUMMARY OF THE INVENTION

In one aspect, the present invention provides methods for separating sperm cells from an aqueous sample. The aqueous sample is contacted with a non-aqueous liquid having a density of greater than about 1.00 g/cm$^3$ and having a density sufficiently low to permit pelleting of at least a portion of the sperm cells in the sample. A force is applied to the contacted sample for a period of time sufficient to form an aqueous layer, a non-aqueous layer, and a sperm cell pellet.

In another aspect, the present invention provides kits for isolating sperm cells from an aqueous sample. A kit according to the present invention includes a non-aqueous liquid having a density of greater than about 1.00 g/cm$^3$ and having a density sufficiently low to permit pelleting of at least a portion of the sperm cells in the sample. Optionally, the kit may include an aqueous solvent, a protease, a chaotropic agent, or a protocol for isolating sperm cells.

DETAILED DESCRIPTION OF THE INVENTION

Figure 1:
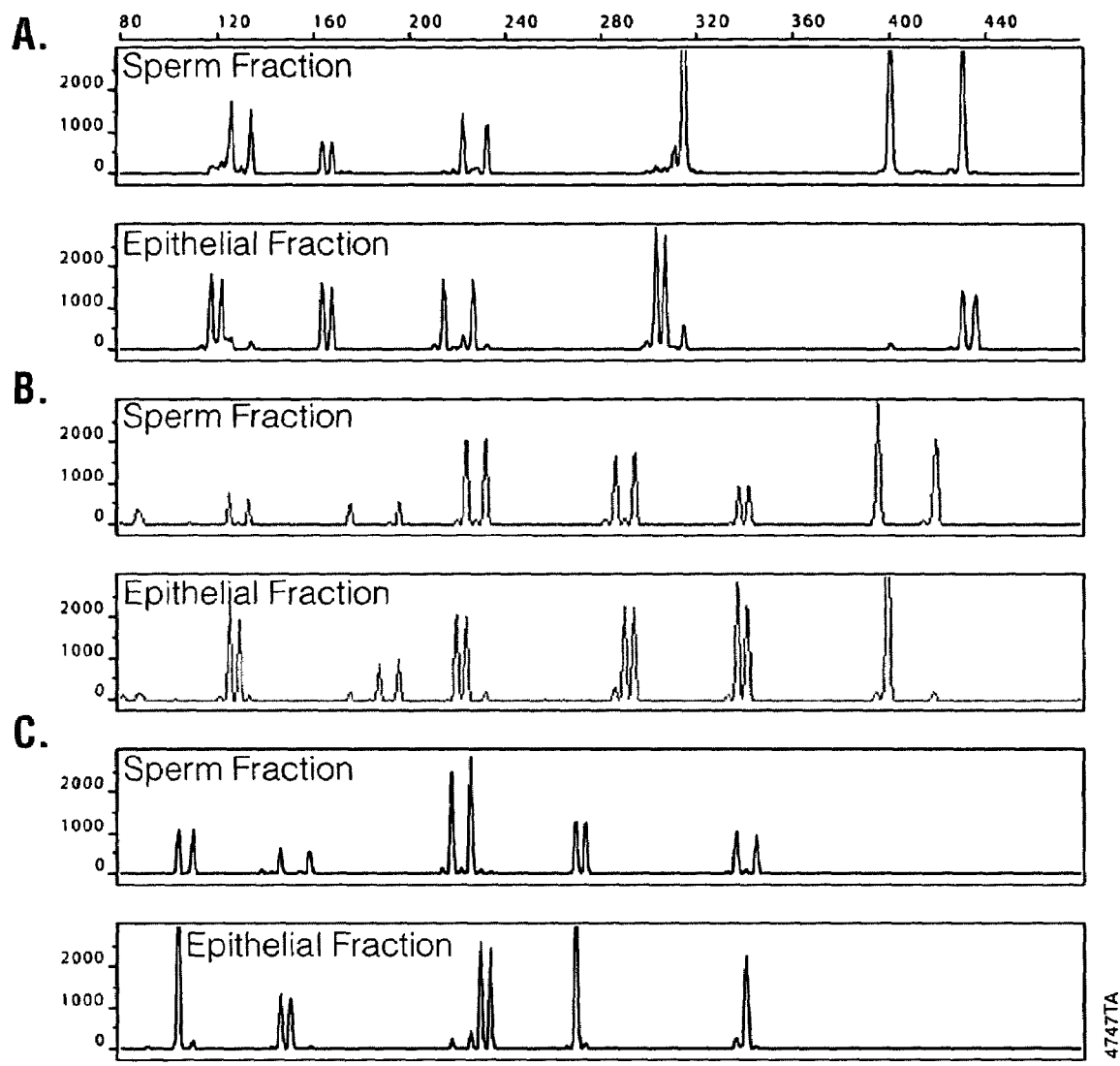
FIG. 1 is an electropherogram of amplified DNA isolated from sperm cells or epithelial cells separated by the method of the invention.

Forensic samples obtained from victims of sexual assault typically contain a large number of epithelial cells and, if present, relatively few sperm cells. In order to obtain DNA from the sperm cells for subsequent use in genetic identity testing, it is necessary to isolate the sperm cells from aqueous soluble material, especially DNA, that may interfere with or complicate the interpretation of results. For example, DNA from lysed epithelial cells is soluble in aqueous solutions.

Briefly, the method of the present invention involves contacting an aqueous sample comprising sperm cells and material soluble in an aqueous solution with a non-aqueous liquid having a density that is greater than that of water but less than that of sperm cells, and pelleting the sperm cells. Suitably, the sperm cells are pelleted by centrifugation. The aqueous soluble material (e.g., DNA) remains in the aqueous phase and is physically separated from the pelleted sperm cells by the non-aqueous phase. As used herein, "sperm cells" may include an intact sperm cell or essentially intact sperm cell, and a sperm cell that has lost its flagellum or "tail". Although a sperm cell may have been exposed to environmental conditions, mechanical sheering, or chemical treatment (e.g., exposure to Proteinase K or other agents) that altered the cell, such cells are within the scope of the invention, especially those cells that retain their nuclei.

Forensic samples from sexual assault victims are typically collected on a solid support, such as a swab or cloth (e.g., a cutting from clothing containing a semen stain). The swab or cloth may be transferred to a container such as a test tube or other suitable container and contacted with an aqueous solution such as a lysis buffer. As described in the Examples, recovery of the aqueous buffer and sperm cells may be facilitated by transferring the solid support and aqueous buffer to a second container equipped with a mechanical barrier that effectively prevents passage of the solid support while allowing the liquid sample to pass and centrifuging to recover the aqueous sample. The second container held a non-aqueous liquid so that removal of the aqueous sample from the solid support and pelleting of sperm cells through a non-aqueous liquid was accomplished in a single centrifugation. Alternatively, the treatment with the non-aqueous liquid could be performed in the same container in which the solid support was treated with the lysis buffer by contacting the aqueous sample with the non-aqueous liquid either before or after removing the solid support. After adding the non-aqueous liquid, the container may be optionally fitted with a mechanical barrier, onto which the solid support is placed prior to centrifugation. In another approach, the sperm cells in the aqueous sample may be pelleted by centrifugation prior to contacting the sample with a non-aqueous liquid. Addition of the non-aqueous liquid will float the aqueous sample off of the pellet and form a barrier (i.e., a non-aqueous layer) between the sperm cell pellet and soluble DNA in the aqueous sample. The latter approach would allow physical separation between pelleted sperm cells and soluble DNA, but would be less effective separating the sperm cell pellet from cellular debris than the other approaches in which the aqueous sample is contacted with the non-aqueous liquid prior to centrifugation.

The lysis buffer suitably comprises Proteinase K, and Sarkosyl or SDS. Optionally, the lysis buffer may comprise any suitable water soluble dye (e.g., FD & C Yellow) to enhance visualization of the aqueous phase. The material is treated with a suitable amount of a protease, such as Proteinase K (270 μg/ml), under conditions that allow lysis of the epithelial cells, but do not promote lysis of the sperm cells. Sperm cells are relatively resistant to proteases because the exposed proteins contain a relatively large number of disulfide bonds. Therefore, reducing conditions are not suitable for differential lysis because the presence of reducing agents would disrupt the disulfide bonds and increase lysis of sperm cells treated with proteases.

After treatment with the protease and detergent, the lysate containing the lysed epithelial cells and intact sperm cells is contacted with a non-aqueous liquid. A suitable non-aqueous liquid may include any non-aqueous liquid having a density greater than that of water but less than that of sperm cells, suitably having a density of greater than 1.00 g/cm$^3$ and having a density sufficiently low to permit at least a portion of the sperm cells to be pelleted. As demonstrated in the Examples below, a non-aqueous liquid having a density of less than 1.29 g/cm$^3$ was found to allow recovery of sperm cells for subsequent DNA isolation, amplification, and analysis. However, it is envisioned that non-aqueous liquids having a density of greater than 1.29 g/cm$^3$ may be used in the method of the invention, provided that the density is sufficiently low to permit at least some of the sperm cells to be pelleted. It is well within the ability of one skilled in the art to evaluate the suitability of non-aqueous liquids to isolate sperm cells according to the method of the invention. The non-aqueous liquid is suitably non-chaotropic so as to prevent undesired lysis of the sperm cells. The non-aqueous liquid is preferably one that has a relatively low solubility in water. Using a non-aqueous liquid having low solubility in water will typically afford better phase separation and reduced contamination of the sperm cell pellet with water soluble materials, such as epithelial cell DNA.

The non-aqueous liquids diethyl glutarate ("DEG"), dimethyl glutarate ("DMG"), and 1-chloro-2-methyl-2-propanol have been evaluated and were found to be useful in the practice of the invention when used alone or in combination. Optionally, the density of the non-aqueous liquid may be adjusted by using two or more non-aqueous liquids having different densities in combination at ratios effective to obtain the desired density. When two or more non-aqueous liquids are used, the liquids are suitably substantially miscible with each other so as to form a liquid mixture of substantially uniform density.

Each of DEG, which has a density of approximately 1.02 g/cm$^3$, 1-chloro-2-methyl-2-propanol, which has a density of about 1.058 g/cm$^3$, and DMG, which has a density of 1.09 g/cm$^3$, afforded acceptable separation of sperm cells from the soluble epithelial cell DNA when used as the sole non-aqueous liquid. DEG may be used in combination with DMG at ratios effective to provide a mixed non-aqueous liquid intermediate between 1.02 g/cm$^3$ and 1.09 g/cm$^3$. In the Examples below, a mixed liquid comprising DEG and DMG in a ratio of about 50:50 was used to obtain a non-aqueous liquid with a density of about 1.055 g/cm$^3$, which was found to afford effective separation between the sperm cell pellet and aqueous soluble epithelial cell DNA. In addition, mixed liquids prepared from DEG and DMG in ratios of from about 100:0 to about 0:100 DEG:DMG were found to be effective in the practice of the invention. We have evaluated the efficacy of various ratios of DEG and DMG and found ratios of 100:0, 50:50, 40:60, 30:70, 20:80, and 0:100 DEG:DMG to be effective in obtaining sufficient quantities of sperm cells of acceptable purity using the methods of the invention.

In addition, we discovered that DMG can be used in combination with chloroform to obtain a mixed non-aqueous liquid of various densities. Mixed liquids of DMG and chloroform are effective in isolating sperm cells at densities of 1.29 g/cm$^3$ or lower. Using mixed liquids containing DMG:chloroform in a ratio of 95:5 and having a density of about 1.108 g/cm$^3$, sperm cell yields were comparable to those obtained with DMG alone. A mixed liquid containing DMG:chloroform in a ratio of 75:25 and having density of 1.189 g/cm$^3$ afforded a lower sperm cell yield than DMG alone. A mixed liquid containing DMG:chloroform in a ratio of 50:50 and having density of 1.29 g/cm$^3$ gave low but detectable levels of sperm cells. In other words, the tested combinations of nonaqueous liquids, having densities of 1.29 g/cm$^3$ or lower, were effective in yielding sperm cell DNA in a yield and of a purity sufficient to permit amplification and genetic identity testing. It is specifically envisioned that chloroform could be used in conjunction with DEG or 1-chloro-2-methyl-2-propanol to isolate sperm cells by selecting appropriate ratios to provide a mixed non-aqueous liquid having a suitable density.

As one skilled in the art will appreciate, a mixed non-aqueous liquid having a relatively low ratio of DEG to DMG will have a relatively high density, and mixed non-aqueous liquids having a relatively high ratio of DEG to DMG will have a relatively low density. It is expected that a non-aqueous liquid having a relatively low density may afford greater recovery of sperm cells, whereas a relatively high density may result in the recovery of fewer sperm cells with less contaminating unlysed epithelial cells and cell debris. Therefore, depending on the application, ratios of various non-aqueous liquids may be adjusted to affect greater recovery of sperm cells or recovery of fewer sperm cells of higher purity.

After contacting the aqueous sample comprising lysed epithelial cells with the non-aqueous liquid, the sample is subjected to a force for a period of time effective to cause separation of the aqueous and non-aqueous phases and pelleting of the sperm cells. Preferably, the force is applied to the sample by centrifuging the sample. Optionally, a spin basket may be employed in the centrifugation step to allow removal of the cells and solution from the solid support.

Epithelial cell DNA, which is soluble in water, is found in the aqueous layer, and insoluble epithelial cell debris, which may also contain trapped epithelial cell DNA, is found at the interface between the aqueous and non-aqueous layers, depending on the density of the non-aqueous liquid. The epithelial cell DNA and cell debris is removed by removing the aqueous layer and interface region, which can be achieved by any suitable means, including pipetting. The epithelial cell DNA present in the aqueous phase may be used as a control in genetic identity testing to confirm the source of the sample. Following recovery of the aqueous phase, a small amount of aqueous solution may remain at or near the surface of the non-aqueous phase and on the container wall. Optionally, to enhance removal of the aqueous solution and epithelial cell DNA without disrupting the sperm cell pellet, the residual aqueous solution may be removed by first layering water or a suitable aqueous solution onto the non-aqueous phase and then removing the aqueous phase. Because water does not mix with the non-aqueous liquid, there is no need to centrifuge the solutions to effect separation of the aqueous and non-aqueous layers.

Following removal of the aqueous phase, a lysis buffer containing a chaotropic agent and a reducing agent may be added to the non-aqueous liquid and vortexed to form a substantially homogenous mixture. As shown in Example 2, a lysis buffer containing guanidine thiocyanate (GTC) and dithiothreitol (DTT) was combined with the non-aqueous phase and sperm cell pellet to effect lysis of the sperm cells. Example 2 further demonstrates that a resin capable of binding DNA can then be added to the sperm cell lysate to purify the DNA from other cellular material.

Alternatively, as described in Example 3, both the aqueous and non-aqueous layers may be removed to leave a sperm cell pellet, and the sperm cells present may be lysed by contacting the cells with an aqueous solution comprising a detergent, such as sodium dodecyl sulfate (SDS) (1% w/v) and DTT, followed by extraction with phenol:chloroform.

It is specifically envisioned that, following removal of the aqueous phase, the sperm cell pellet and the non-aqueous phase could be extracted with phenol:chloroform and an aqueous solution containing a detergent (e.g., SDS or Sarkosyl) to effect release of the sperm cell DNA.

As described in the Examples, the method of the invention was found to be effective in isolating sperm cells from epithelial cells contained within forensic samples such as vaginal or cervical swabs. It is envisioned that the method will be useful in isolating sperm cells from other sources, including other solid supports containing semen, such as cloth. It is reasonably expected that the method of the invention will be suitable for use with samples containing sperm cells and contaminating red or white blood cells or DNA derived from nucleated non-sperm cells.

The method of the invention is expected to have general applicability in separating cells on the basis of their differential densities, or to facilitate isolation of other cell types from material soluble in an aqueous solvent following selective lysis. It is also envisioned that the method may be suitable for isolating various sub-cellular organelles.

The following non-limiting examples are intended to be purely illustrative.

EXAMPLE 1

Isolation of Sperm Cells from Samples Containing Epithelial Cells

Samples used in evaluating sperm cell isolation included a fresh buccal swab containing added semen, fresh or four year old vaginal samples containing added semen, and a four year old 11-hour post coital vaginal sample. The solid support (e.g., a swab) containing the samples were placed in a microcentrifuge tube. A 0.5 ml aliquot of a digestion solution containing 50 mM NaCl, 10 mM Tris, pH 8.0, 10 mM EDTA, 0.2% SDS, FD&C Yellow dye, and 270 µg/ml Proteinase K was added to each sample. The tubes containing the samples were vortexed for 30 seconds and incubated at 56° C. for 1 hour. Diethyl glutarate and dimethyl glutarate were combined at ratios of 100:0, 50:50, 40:60, 30:70, 20:80, and 0:100 DEG:DMG to form mixed non-aqueous liquids. The ratio of 50:50 formed a liquid with a density of about 1.055 g/cm$^3$. A 100 µl aliquot of the non-aqueous liquid including ratios of 100:0, 50:50, 40:60, 30:70, 20:80, or 0:100 DEG:DMG was transferred to a clean microcentrifuge tube fitted with a spin basket. Following the incubation, the Proteinase K digestion reaction and the solid support were transferred to the spin basket. The spin basket and microcentrifuge tube were placed in a microcentrifuge and centrifuged for 10 min at 14,000 rpm (10,000×g). The yellow aqueous phase and any cellular debris near the boundary between the aqueous and non-aqueous phases was removed by pipetting. A 100 µl aliquot of water was layered onto the top of the non-aqueous phase, and allowed to stand for about 30 seconds before removing the aqueous phase with a pipette.

In addition, sperm cells were isolated using ratios of dimethyl glutarate and chloroform for the non-aqueous solution. Dimethyl glutarate and chloroform were combined in the ratios of 95:5, 75:25 and 50:50 dimethyl glutarate:chloroform. The density of the 50:50 mixture was 1.290.

EXAMPLE 2

Isolation of DNA from Sperm Cells or Lysed Epithelial Cells Using Chaotropic Salt and Reducing Conditions The DNA from the sperm cell pellet of Example 1 was isolated according to DNA isolation methods described in Promega Technical Bulletin TB296 using components provided in the DNA IQ™ system (Promega Corp., Madison, Wis. Cat. No. DC6701). A 200 µl aliquot of DNA IQ™ lysis buffer containing 4.5 M guanidine thiocyanate (GTC) and 10 mM dithiothreitol (DTT) was added to the microfuge tube containing the non-aqueous liquid and sperm cell pellet, and vortexed briefly to disrupt the sperm cell pellet and to form a homogenous mixture of the non-aqueous phase and the lysis buffer.

A 7 µl aliquot of DNA IQ™ Resin was added to the solution and mixed by vortexing at high speed for 3 seconds and incubated at room temperature for 5 minutes. The mixture was vortexed for 2 seconds at high speed, the tube was placed in a magnetic stand, and after the paramagnetic resin was attracted to the side of the tube, the homogeneous mixture of lysis buffer and non-aqueous liquid was removed and discarded. The particles were washed three times with 100 µl aliquots of DNA IQ™ Wash Buffer. The particles were contacted with 40 µl of DNA IQ™ Elution Buffer, vortexed at high speed for two seconds, and incubated at 65° C. Immediately following incubation at 65° C., the tube was vortexed for 2 seconds at high speed, placed in a magnetic stand, and the eluate was transferred to a clean container.

Epithelial cell DNA was isolated in the same manner that DNA from lysed sperm cells was isolated, as described in the preceding paragraph.

EXAMPLE 3

Isolation of DNA from Sperm Cells Using a Detergent and Phenol:Chloroform Extraction The DNA from the sperm cell pellet of Example 1 was isolated by first removing the non-aqueous liquid to leave a firm sperm cell pellet. A 300 µl solution containing 10 mM Tris, pH 8.0, 1 mM EDTA, 10 mM DTT, and 1% SDS was added to the sperm cell pellet, and the tube was vortexed to lyse the sperm cells and dissolve the DNA. An equal volume of phenol:chloroform (1:1, v/v) was added and vortexed to denature the protein. The aqueous DNA-containing solution was removed, concentrated in a Microcon® apparatus, washed with 200 µl of a buffer containing 10 mM Tris, pH 8.0, 0.1 mM EDTA, and concentrated again in the Microcon® apparatus to about 40 µl. The purified DNA was transferred to a clean container.

EXAMPLE 4

Characterization of Sperm Cell DNA Following Multiplex Amplification

Following recovery of DNA from isolated sperm cells or lysed epithelial cells, according to Example 2 or Example 3, DNA was amplified using PowerPlex® 16 (Promega Corp., Madison, Wis. Cat. # DC6530). The amplified DNA was then analyzed using an ABI Prism® 310 Genetic Analyzer.

Representative results are provided in the electropherogram shown in FIG. 1. With reference to FIG. 1, DNA was isolated from sperm cells or epithelial cells as described above in Examples 1 and 2 from a vaginal swab containing sperm cells and stored at room temperature for 4 years. Following DNA purification from the epithelial cell lysate or the sperm cell lysate by the DNA IQ™ system, DNA (1/400$^{th}$ of the epithelial cell fraction and 1/80$^{th}$ of the sperm cell fraction) was amplified using PowerPlex® 16 and amplification products were analyzed using the ABI Prism® 310 Genetic Analyzer. The electropherogram of FIG. 1 shows amplification products in the Fluoroscein channel (FIG. 1A); shows amplification products in the JOE channel (FIG. 1B); and amplification products in the TMR channel (FIG. 1C). The results are separated according to dye color to permit one to more easily identify each of the 16 loci, and the results from the sperm cell DNA are shown just above the results obtained from the epithelial cell DNA.

As can be seen from FIG. 1, the method provides separation of sperm cells from epithelial cells, as is evidenced by the very low levels of contaminating epithelial cell DNA in the sperm cell DNA. Only minor sperm cell DNA is seen in the epithelial cell DNA fraction and is likely due to sperm cell lysis during prolonged storage at room temperature.

What is claimed is:

1. A method of separating sperm cells from an aqueous sample comprising:

(a) contacting the aqueous sample with a non-aqueous liquid comprising at least one of diethyl glutarate, dimethyl glutarate, and 1-chloro-2-methyl-2-propanol and having a density greater than about 1.00 g/cm$^3$, wherein the density of the non-aqueous liquid is sufficiently low to permit pelleting of at least a portion of the sperm cells in the sample;

(b) applying a force to the contacted sample for a period of time sufficient to form an aqueous layer, a non-aqueous layer, and a sperm pellet thus seperating sperm cells from an aqueous sample.

2. The method of claim 1, wherein the force is applied by centrifugation.

3. The method of claim 1, wherein the non-aqueous liquid comprises diethyl glutarate.

4. The method of claim 1, wherein the non-aqueous liquid comprises dimethyl glutarate.

5. The method of claim 1, wherein the non-aqueous liquid comprises diethyl glutarate and dimethyl glutarate.

6. The method of claim 5, wherein the non-aqueous liquid comprises diethyl glutarate and dimethyl glutarate in a ratio in the range of about 99.9:0.1, diethyl glutarate to dimethyl glutarate, to about 0.1:99.9 diethyl glutarate to dimethyl glutarate.

7. The method of claim 1, wherein the non-aqueous liquid has a density of at least about 1.01 g/cm$^3$.

8. The method of claim 1, wherein the non-aqueous liquid has a density of about 1.29 g/cm$^3$ or lower.

9. The method of claim 1, wherein the non-aqueous liquid further comprises chloroform.

10. The method of claim 9, wherein the non-aqueous liquid comprises chloroform and dimethyl glutarate in a ratio of from about of 0.1:99.9 to about 50:50 dimethyl glutarate:chloroform.

11. The method of claim 1, wherein the non-aqueous liquid has a density in the range of from about 1.02 g/cm$^3$ to about 1.29 g/cm$^3$.

12. The method of claim 1, wherein the non-aqueous liquid has a density in the range of from about 1.050 g/cm$^3$ to about 1.058 g/cm$^3$.

13. The method of claim 1, wherein the aqueous sample comprises lysed epithelial cells.

14. The method of claim 1, further comprising the step of:

(c) removing the aqueous layer.

15. The method of claim 14, further comprising the step of:

(d) contacting the non-aqueous layer and sperm pellet with a chaotropic agent.

16. The method of claim 15, wherein the chaotropic agent comprises a chaotropic salt.

17. The method of claim 15, wherein the chaotropic agent comprises a detergent, and further comprising the step of:

(e) contacting the non-aqueous layer and sperm pellet of step (d) with phenol:chloroform.

18. The method of claim 14, further comprising the step of:

(d) removing the non-aqueous layer.

19. The method of claim 18, further comprising the step of:

(e) contacting the sperm pellet of step (d) with an aqueous detergent and phenol:chloroform.

* * * * *